US00PP21830P3

(12) United States Plant Patent
Scheffers

(10) Patent No.: US PP21,830 P3
(45) Date of Patent: Mar. 29, 2011

(54) *DRACAENA* PLANT NAMED "2004027J"

(50) Latin Name: *Dracaena fragrans*
Varietal Denomination: 2004027J

(76) Inventor: Ruud Scheffers, Honselersdijk (NL)

( * ) Notice: Subject to any disclaimer, the term of this patent is extended or adjusted under 35 U.S.C. 154(b) by 0 days.

(21) Appl. No.: 12/455,728

(22) Filed: Jun. 6, 2009

(65) Prior Publication Data

US 2010/0313319 P1 Dec. 9, 2010

(51) Int. Cl.
*A01H 5/00* (2006.01)

(52) U.S. Cl. ..... Plt./383

(58) Field of Classification Search ..... Plt./383
See application file for complete search history.

(56) References Cited

PUBLICATIONS

Upov Plant variety Database 2010/02 search for cultivar 2004027J, p. 1.*

* cited by examiner

*Primary Examiner*—Annette H Para

(57) ABSTRACT

A new and distinct *Dracaena fragrans* cultivar named '2004027J' is disclosed, characterized by broad, short foliage, of a dark green color, and yellow margin. The new variety is a *Dracaena,* and is normally used as an indoor ornamental plant.

1 Drawing Sheet

Figure 1:
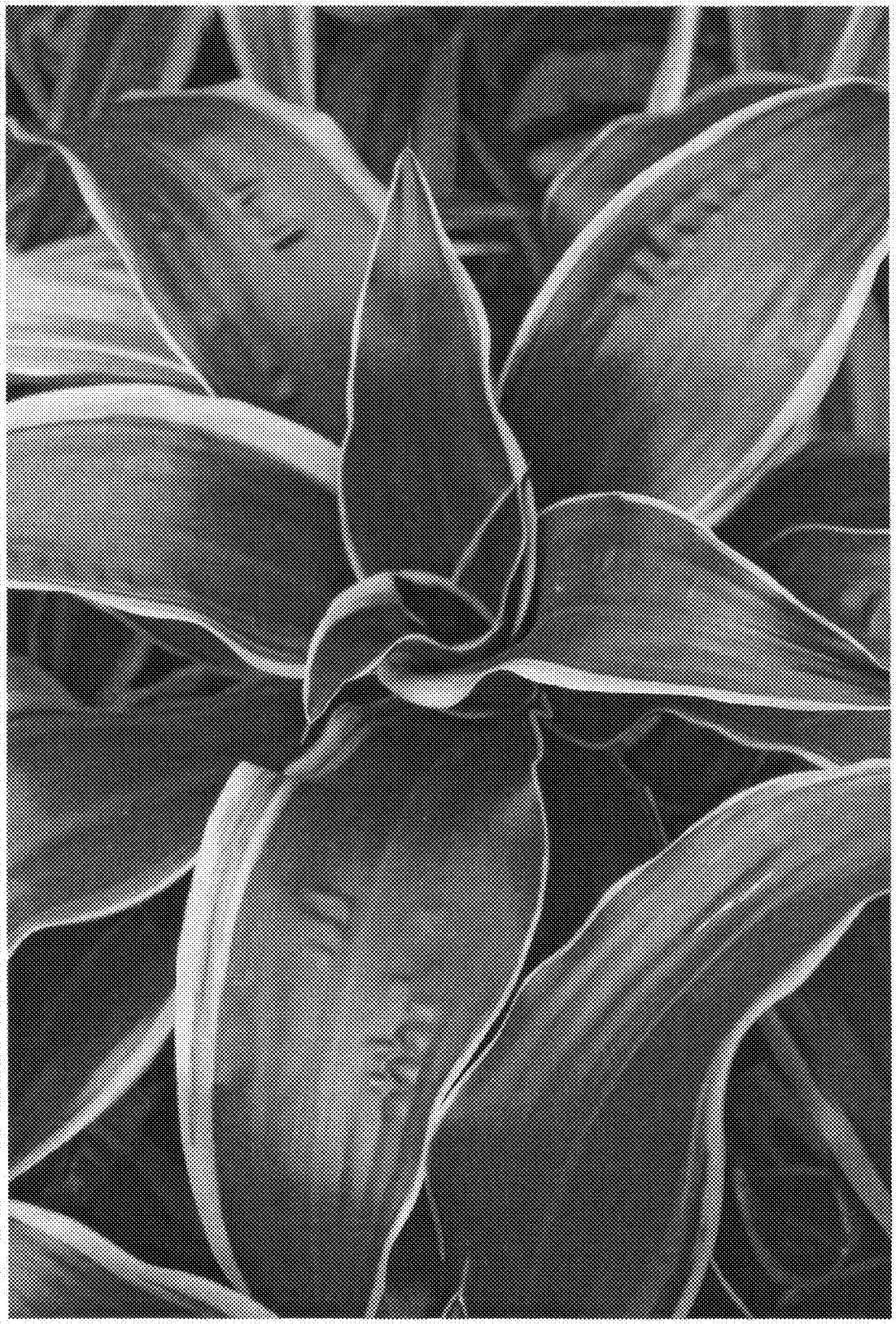

Latin name of the genus and species: *Dracaena fragrans.*
Variety denomination: '2004027J'.

BACKGROUND OF THE INVENTION

The new cultivar was discovered as a chance, single stem mutation in a commercial nursery in Honselersdijk, The Netherlands. The inventor, Ruud Scheffers, a citizen of The Netherlands, discovered the new variety as a single stem mutation occurring on plants of the patented commercial variety, *Dracaena fragrans* 'Lemon Surprise' U.S. Plant Pat. No. 12,654. The new variety was discovered during the Spring of 2002 by the inventor.

Asexual reproduction of the new cultivar '2004027J' by vegetative cuttings was first performed at a commercial nursery in Honselersdijk, The Netherlands, during the Summer of 2002. The inventor has tested reproduction of the new variety extensively for the purposes of stability. Many generations have been reproduced, and have shown that the unique features of this cultivar are stable and reproduced true to type through successive generations.

SUMMARY OF THE INVENTION

The cultivar '2004027J' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '2004027J.' These characteristics in combination distinguish '2004027J' as a new and distinct *Dracaena fragrans* cultivar:

1. Broad, short foliage.
2. Dark green foliage color with yellow margin.

PARENT COMPARISON

Plants of the new cultivar '2004027J' are similar to plants of the parent variety *Dracaena fragrans* 'Lemon Surprise' in most horticultural characteristics. However, plants of the new cultivar '2004027J' produce shorter, wider leaves with a different color pattern. Additionally, plants of the new variety are less compact than 'Lemon Surprise'.

The parent variety is also the most similar commercial comparisons to the new cultivar.

BRIEF DESCRIPTION OF THE PHOTOGRAPH

The accompanying photograph in FIG. 1 illustrates in full color a typical plant of '2004027J' grown in a greenhouse. The pot size is a commercial 20 cm container, approximately. The plant shown is approximately 1 year old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe '2004027J' plants grown in a commercial greenhouse in Honselersdijk, The Netherlands. The growing temperature ranged from approximately 20 to 21° C. at night and 20 to 22° C. during the day. Measurements and numerical values represent averages of typical flowering types. No chemical or photoperiodic treatments were given.

Botanical classification: *Dracaena fragrans* '2004027J.'

PROPAGATION

Time to rooting: About 3 weeks at approximately 20 to 22° C.
Root description: Small, fleshy, free-branching roots.

PLANT

Age of plant described: Approximately 1 year.
Pot size of plant described: Approximately 20 cm.

Growth habit: Upright, tender perennial, suitable for indoor ornamental use.
Height: Approximately 22.4 cm.
Plant spread: Approximately 37.8 cm.
Growth rate: Moderate. Approximately 8 cm per month.
Branching characteristics: One main stem, otherwise, infrequent basally branching.
Diameter of stem: Approximately 4 cm.
Internode length: Average 1.1 cm.
Texture of stems: Rounded, smooth, matte.
Color of stems: Near RHS Green 145B.
Stem strength: Very strong.
Number of leaves per stem: Average 14.

FOLIAGE

Leaf:

*Arrangement.*—Alternate, spiraling.
*Average length.*—Approximately 23.6 cm.
*Average width.*—Approximately 5.9 cm.
*Shape of blade.*—Lorate.
*Aspect.*—Arching.
*Apex.*—Acute.
*Base.*—Sheathing.
*Attachment.*—Sessile.
*Margin.*—Entire.
*Texture of top surface.*—Smooth, glossy, leathery. Irregularly ribbed.
*Texture of bottom surface.*—Smooth, glossy, leathery.
*Color.*—Young foliage upper side: Near RHS Green N137C, Yellow-Green 144A towards the base, margins yellow-green 150B, average width of marginal coloration: 2 mm. Young foliage under side: Near RHS Yellow-Green 146A, lighter towards the base, base coloration near 144C, margins Yellow-Green 150B, average width of marginal coloration: 2 mm. Mature foliage upper side: Near RHS Green 139A but darker, margins Yellow-Green 144B, average width of marginal coloration: 2 mm. Mature foliage under side: Near RHS Yellow-Green 146A but slightly darker, margins Yellow-Green 144B, average width of marginal coloration: 2 mm.
*Venation.*—Type: Parallel. Color: Indistinguishable from leaf blade color.

Petiole: No petioles, sessile.

FLOWER

Flowering not observed to date.

OTHER CHARACTERISTICS

Disease resistance: Neither resistance nor susceptibility to diseases or pests normal to *Dracaena* has been observed in this variety.
Drought tolerance and temperature tolerance: Tender perennial, low temperature damage occurs near 5° C. Tolerates high temperature to at least 35° C. No drought tolerance has been observed.
Fruit/seed production: Fruits and seeds have not been observed.

What is claimed is:

1. A new and distinct cultivar of *Dracaena* plant named '2004027J' as herein illustrated and described.

* * * * *